(12) United States Patent
Patel et al.

(10) Patent No.: US 12,194,241 B2
(45) Date of Patent: Jan. 14, 2025

(54) NASOPHARYNGEAL AIRWAY SYSTEM DEVICE

(71) Applicants: Ketan Patel, Plymouth, MN (US); Paul Colligan, Rogers, MN (US)

(72) Inventors: Ketan Patel, Plymouth, MN (US); Paul Colligan, Rogers, MN (US)

(*) Notice: Subject to any disclaimer, the term of this patent is extended or adjusted under 35 U.S.C. 154(b) by 0 days.

(21) Appl. No.: 18/429,915

(22) Filed: Feb. 1, 2024

(65) Prior Publication Data
US 2024/0261526 A1  Aug. 8, 2024

Related U.S. Application Data

(60) Provisional application No. 63/442,945, filed on Feb. 2, 2023.

(51) Int. Cl.
*A61M 16/06* (2006.01)
*A61M 25/00* (2006.01)

(52) U.S. Cl.
CPC ..... *A61M 16/0672* (2014.02); *A61M 25/0097* (2013.01); *A61M 2210/065* (2013.01)

(58) Field of Classification Search
CPC .......... A61M 16/0666; A61M 16/0672; A61M 16/0461; A61M 16/0486; A61M 16/085
See application file for complete search history.

(56) References Cited

U.S. PATENT DOCUMENTS

| | | | |
|---|---|---|---|
| 9,814,854 B2 | 11/2017 | Chua | |
| 10,398,869 B2 | 9/2019 | Khabiri et al. | |
| 10,695,517 B2 | 6/2020 | Lei | |
| 2004/0231675 A1 | 11/2004 | Lyons | |
| 2012/0118286 A1 | 5/2012 | Barodka | |
| 2015/0320957 A1 | 11/2015 | Wei | |
| 2017/0095630 A1 | 4/2017 | Yeatts | |
| 2017/0203070 A1* | 7/2017 | Lei | A61M 16/0666 |
| 2020/0384226 A1 | 12/2020 | Higgins et al. | |
| 2021/0016040 A1 | 1/2021 | McGann et al. | |
| 2021/0030986 A1 | 2/2021 | Reightler | |

FOREIGN PATENT DOCUMENTS

| | | |
|---|---|---|
| KR | 101915929 B1 | 11/2018 |
| WO | 2014078035 A1 | 5/2014 |

OTHER PUBLICATIONS

Airway Management, 2015, Clinical Gate, p. 9 (Year: 2015).*

* cited by examiner

*Primary Examiner* — Margaret M Luarca
(74) *Attorney, Agent, or Firm* — Bold IP PLLC; Binita Singh

(57) ABSTRACT

A nasopharyngeal airway device is provided to be used in conjunction with an oxygen source and a capnometer. In one or more non-limiting embodiments, the nasopharyngeal airway device provides adequate oxygen delivery and monitors capnography output more efficiently. The device includes a nasal trumpet having one or more lumens, and a nasal cannula having a tube portion and at least two prongs. A first prong is insertable into a nasal cavity of a human subject, wherein the remaining prongs are equal in number to a number of one or more lumens of the nasal trumpet. The remaining prongs are adjacent to each other on the tube portion and configured to snugly fit into the nasal trumpet. The gases may pass into the nasal cannula from their respective ends into the prongs which may be separated by a single closure in the cannula so as to prevent the mixture of gasses.

20 Claims, 8 Drawing Sheets

NASOPHARYNGEAL AIRWAY SYSTEM DEVICE

CROSS-REFERENCE TO RELATED APPLICATIONS

This application is a non-provisional application which claims priority to U.S. Provisional Application No. 63/442,945 filed on Feb. 2, 2023, which is incorporated by reference in its entirety.

FIELD OF THE DISCLOSURE

The present invention relates to a system and device for sedation monitoring when administering anesthesia versus sedation in a hospital or clinical setting. In particular, the system and device herein relate to embodiments that allow for sedation monitoring using a nasopharyngeal airway device.

BACKGROUND

Annually in the United States, there are about 250 million sedation procedures completed for patients undergoing an endoscopy or a dental procedure in a year. In adhering to best practice standards in sedation, optimal management of the patients during these sedation procedures is imperative. These standards of practice include adhering to the standards for basic anesthetic monitoring developed by the Standards and Practice Parameters Committee (CSPP) of the American Society of Anesthesiologists (ANA), guidelines from the American Association of Nurse Anesthetists (AANA), and recommendations from the Anesthesia Patient Safety Foundation (APSF). Many unique and specific responsibilities need to be considered by providers involved in the management of patients during sedation. Patient selection criteria, adequately trained staff, accessibility to emergency medication and equipment, and abiding by standards of care are all part of providing quality care.

Sedation monitoring comprises of obtaining body temperature, pulse oximetry, electrocardiogram, blood pressure, oxygen analysis when oxygen is delivered through a breathing system, and end-tidal carbon dioxide ($CO_2$) when administering anesthesia. A monitor for the presence of expired carbon dioxide when administering moderate or deep sedation is a standard of care where supplemental oxygen is provided for such patients to their lungs and their exhaled carbon dioxide level (capnography) is monitored.

Currently, such procedures are completed with a nasal cannula device that provides both oxygen and carbon dioxide monitoring at the level of the external nares. Two main issues arise with providing oxygen and accurate carbon dioxide monitoring to a sedated patient during a surgical procedure with a nasal cannula. Firstly, a nasal cannula cannot ensure adequate/predictable airway flow to the lungs, especially through an anatomical barrier, for example a deviated septum that is present in about 70-80% of the population. Secondly, this deviated septum also can hinder the ability to accurately detect carbon dioxide. This altered anatomy has often been bypassed with a nasopharyngeal airway, however, this has the drawback of an inability to detect carbon dioxide or provide a closed system for accurate monitoring.

Accordingly, there is still an unsolved need for sedation monitoring during anesthesia administration using a nasopharyngeal airway device that may address these and other existing issues.

SUMMARY

One or more embodiments are provided below for a nasopharyngeal airway system device. The nasopharyngeal airway system (NPAS) provides the ability for providers administering sedation to abide by the standards of care to monitor end-tidal carbon dioxide and the delivery of supplemental oxygen when needed. The nasopharyngeal device of the present invention addresses the aforementioned drawbacks by providing adequate oxygen delivery through variations of nasal anatomy while predictably monitoring capnography output which isn't currently available through the traditional nasopharyngeal airway devices. The unique connection between the nasal piece and the nasopharyngeal airway addresses both problems of delivering adequate oxygen to the lungs through the nasopharyngeal airway component while the carbon dioxide sensor at the level of the oropharynx and laryngopharynx provides capnography monitoring. The NPAS device inherently implements standards of care surrounding sedation and/or anesthesia.

The NPAS device may be configured in different sizes to address both pediatric and adult nasal airways. The nasopharyngeal device of the present invention is advantageous over current devices as it is beneficial with long sedation cases to execute consistent monitoring, improve quality of care, implement standards of care, and minimize distractions for the provider, allowing increased efficiencies throughout procedures. The NPAS device can also have a cascade effect potentially minimizing delays in trouble shooting monitoring errors, decreasing turnover time between cases, and increasing patient volume by opening up patient selection criteria due to the increased sensitivity of monitoring. This is advantageous to the provider and support staff, and most importantly increases safety for the patient.

Other aspects and advantages of the invention will be apparent from the following description and the appended claims.

BRIEF DESCRIPTION OF THE DRAWINGS

Embodiments of the present disclosure are described in detail below with reference to the following drawings. These and other features, aspects, and advantages of the present disclosure will become better understood with regard to the following description, appended claims, and accompanying drawings. The drawings described herein are for illustrative purposes only of selected embodiments and not all possible implementations and are not intended to limit the scope of the present disclosure.

DETAILED DESCRIPTION

Figure 1:
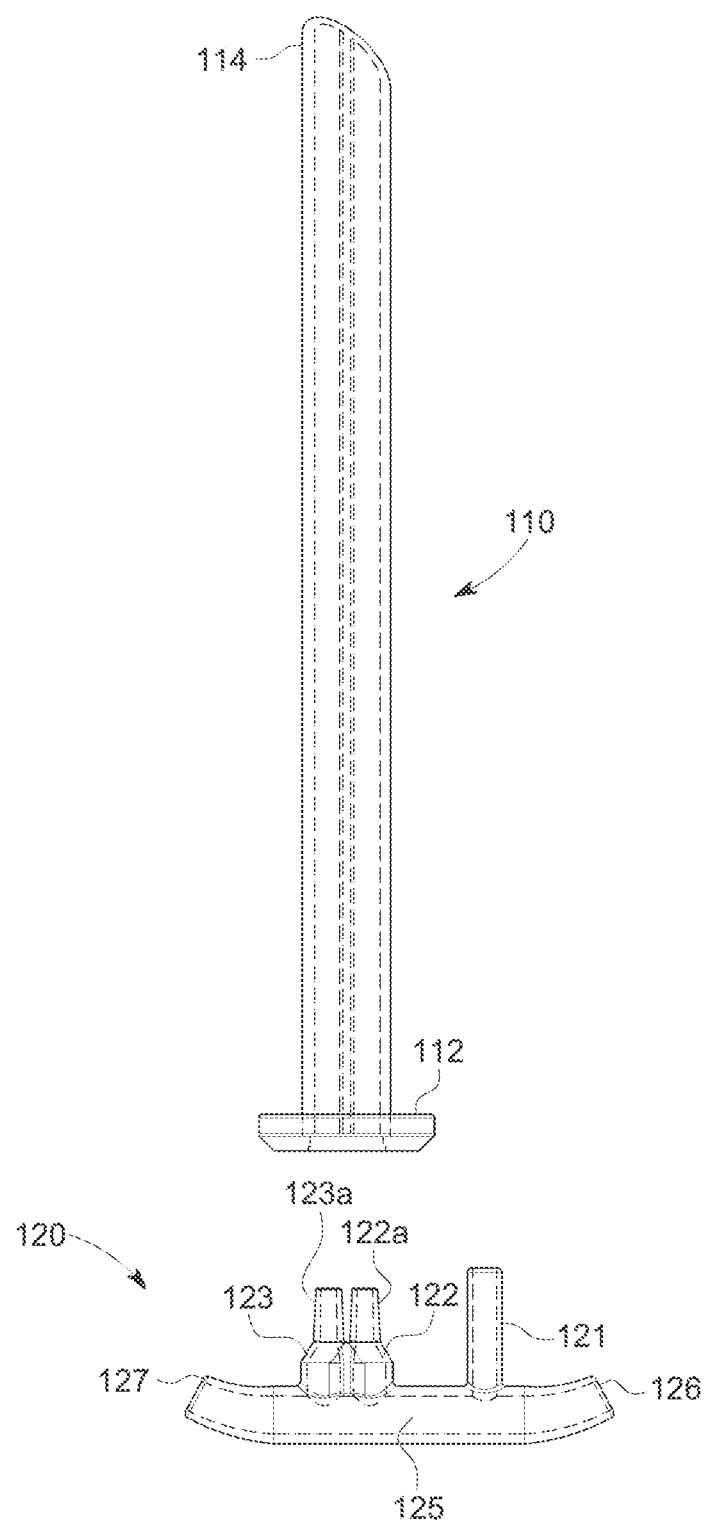
FIG. 1 is a pictorial illustration of an expanded view of a nasopharyngeal airway system in accordance with an illustrative embodiment.

In the Summary above and in this Detailed Description, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The term "comprises" and grammatical equivalents thereof are used herein to mean that other components, ingredients, steps, among others, are optionally present. For example, an article "comprising" (or "which comprises") components A, B, and C can consist of (i.e., contain only) components A, B, and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm and upper limit is 100 mm.

Certain terminology and derivations thereof may be used in the following description for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The term "coupled to" as used herein may mean a direct or indirect connection via one or more components.

The present disclosure is generally drawn to various embodiments for nasopharyngeal airway systems. The use of nasopharyngeal airway systems is required in situations where an artificial form of airway maintenance is necessary and/or where tracheal intubation is impossible, inadvisable, unnecessary, or an additional monitoring device is desired. When a patient becomes unconscious, the muscles in the jaw commonly relax and can allow the tongue to slide back and obstruct the airway, especially in the supine position. This makes airway management necessary by using a device that maintains an open airway. The various embodiments of the nasopharyngeal airway system described in the present invention is one of the available tools to maintain an open airway. In one or more non-limiting embodiments, the present description provides embodiments for a nasopharyngeal airway system that makes it possible to provide adequate oxygen delivery and monitor capnography output. Capnography is a clinical procedure used for the measurement of $CO_2$ levels in respired air at the end of expiration (End Tidal $CO_2$ or ET $CO_2$). In particular, the one or more non-limiting embodiments for a nasopharyngeal airway system device allows a more direct way of monitoring end tidal $CO_2$.

Accordingly, the one or more non-limiting embodiments provided below describe a nasopharyngeal airway device and system used in conjunction with an oxygen source and a capnometer (measures end tidal $CO_2$). The subjects in which the nasopharyngeal airway device and system may be used are human subjects, including both male and female subjects, and including adult and pediatric populations, such as geriatric, adolescent, infant, and neonate. In addition, the nasopharyngeal airway device and system can be modified and adapted for use in animal subjects where sedation and monitoring are utilized in veterinary sciences. Thus, the embodiments provided herein may be fashioned in multiple sizes to accommodate for variations in nasal anatomy including adult and pediatric sizes. Further details are provided below with reference to the Figures.

Figure 2:
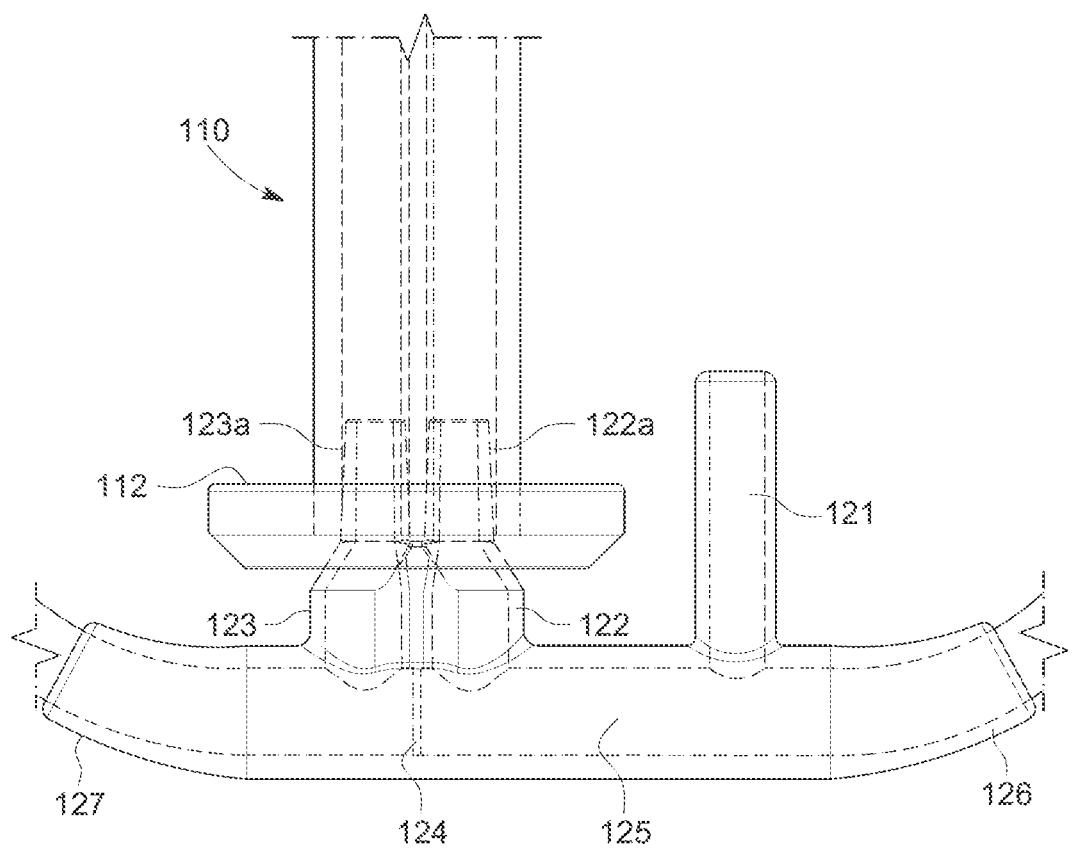
FIG. 2 is a pictorial illustration of an assembled nasopharyngeal airway system from FIG. 1 in accordance with an illustrative embodiment.

Turning to the figures, FIGS. 1 to 7 are pictorial illustrations depicting a nasopharyngeal airway system 100 which is an example of a system for efficiently and adequately providing oxygen and for monitoring end tidal $CO_2$. In one or more non-limiting embodiments, the nasopharyngeal airway system 100 comprises a nasal trumpet 110 and a nasal cannula 120. The nasal trumpet 110 is a tube that is designed to be inserted through a human subject's nasal passage down to the posterior pharynx to secure an open airway. As seen in FIG. 2, the nasal cannula 120 is inserted into the nasal trumpet 110, wherein an oxygen source and a capnometer are connected to the nasal cannula 120.

FIG. 1 illustrates an expanded view of the device 100. Specific attention is drawn to the nasal trumpet 110 which can be defined as having a proximal end 112 and a distal end 114. The proximal end 112 and the distal end 114 are used herein to describe portions of the present invention with respect to when the nasal trumpet 110 is in use, and thus the proximal end 112 is the end that is on an outside of a subject's nasal passageway and the distal end 114 is the end that is inserted into the nasal passageway. The proximal end 112 is like most other nasal trumpets in that the proximal end 112 includes features that are designed to be flared to prevent the nasal trumpet 110 from being inserted fully into a nasal passageway. FIGS. 1, 2, and 5-7 illustrate the proximal end 112 with a flared end, which is an example of a feature which prevents the nasal trumpet from being fully inserted into a nasal passageway. The nasal trumpet 110 is tubular in structure and is dimensioned so that the distal end 114 is insertable through a nasal passageway and into the nasopharynx, preferably the posterior nasopharynx, of a subject. The distal end 114 is shown to have an angled tip (not blunt), such that the insertion of the distal end 114 is easier.

Figure 5:
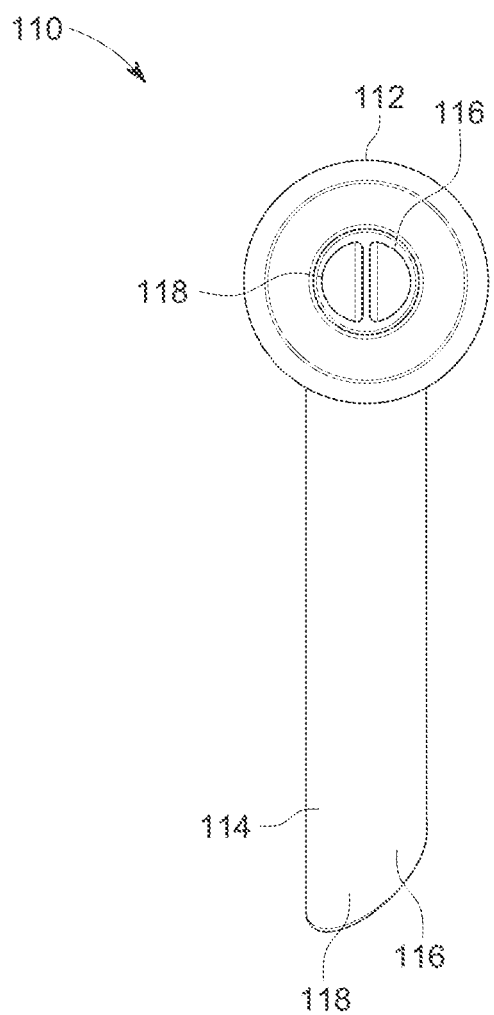
FIG. 5 a pictorial illustration of a front view of a proximal end of a nasal trumpet of the nasopharyngeal airway system in accordance with an illustrative embodiment.
Figure 6:
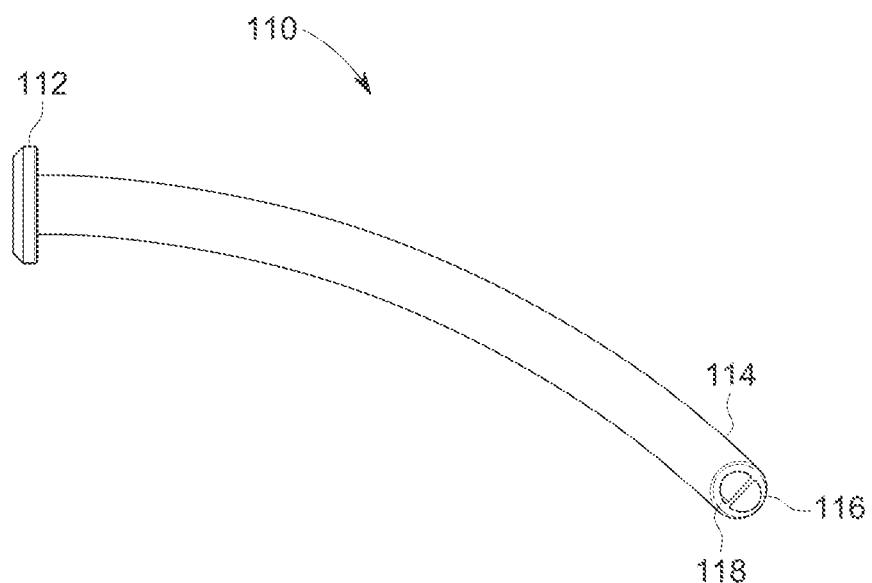
FIG. 6 is a pictorial illustration of a side view of the nasal trumpet in accordance with an illustrative embodiment.
Figure 7:
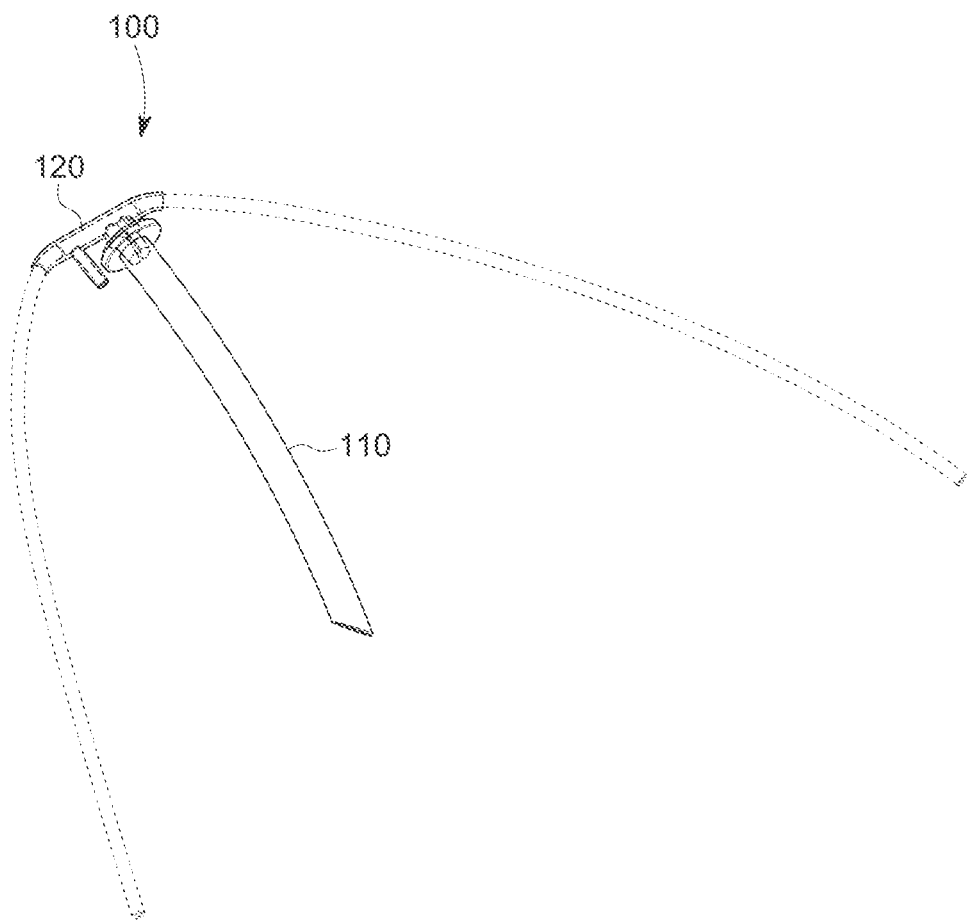
FIG. 7 is a pictorial illustration of a perspective view of the nasopharyngeal airway system in accordance with an illustrative embodiment.

FIG. 5 illustrates a front view of the proximal end 112 of the nasal trumpet 110. FIG. 6 illustrates a side view of the nasal trumpet 110 which provides a front view of the distal end 114 of the nasal trumpet 110. An interior of the nasal trumpet 110 may be divided into two or more lumens. In the figures shown, the interior of the nasal trumpet 110 is divided into two lumens to allow more delivery of oxygen while also detecting $CO_2$. For example, a first lumen 116 delivers oxygen and a second lumen 118 intakes ET $CO_2$. It is to be understood that either side can deliver oxygen and detect ET $CO_2$ and is dependent on the nasal cannula 120 connections to the nasal trumpet 110 and how the external sources are connected to the nasal cannula 120. The figures illustrate the double lumen in the nasal trumpet 110 extending from the proximal end 112 to the distal end 114 to keep the oxygen delivery and the ET $CO_2$ detection separated and prevent dilution. As shown, the first lumen 116 and the second lumen 118 are opposed to each, but it is to be understood that the lumens 116, 118 do not have to be opposed to each other, and further can also be of different lengths, wherein one of the lumens can be longer than the other lumen. The illustrations also show the lumens 116, 118 having a semi-circular geometry and having a similar radius. It is to be understood that the lumens 116, 118 can have different radii. Additionally, the lumens 116, 118 can also be of different shapes and the shape of the lumens can vary between the two. The shapes of the lumens can include, and are not limited to, an oval, a quadrilateral, a triangle, and a polygon.

In one or more non-limiting embodiments, the nasal cannula 120 is a tube that delivers supplemental oxygen to a subject and receives the ET $CO_2$ from the subject to monitor optimal respiration. The nasal cannula 120 has a tube portion 125 which includes two ends, 126, 127 that receive and deliver oxygen and $ETCO_2$. The tube portion 125 has one or more prongs projecting away from the tube portion 125. As seen in one or more non-limiting embodiments in FIGS. 1-4, the nasal cannula 120 includes a first prong 121 that is intended to be inserted into a nostril of a subject, and a second prong 122 and a third prong 123 that are intended to be inserted into the proximal end 112 of the nasal trumpet 110. As seen in the Figures, the second and third prongs 122, 123 are adjoined together, however each have a separate lumen so that the gasses (i.e., oxygen and $CO_2$) do not mix with each other and negatively affect the concentration of each.

Figure 3:
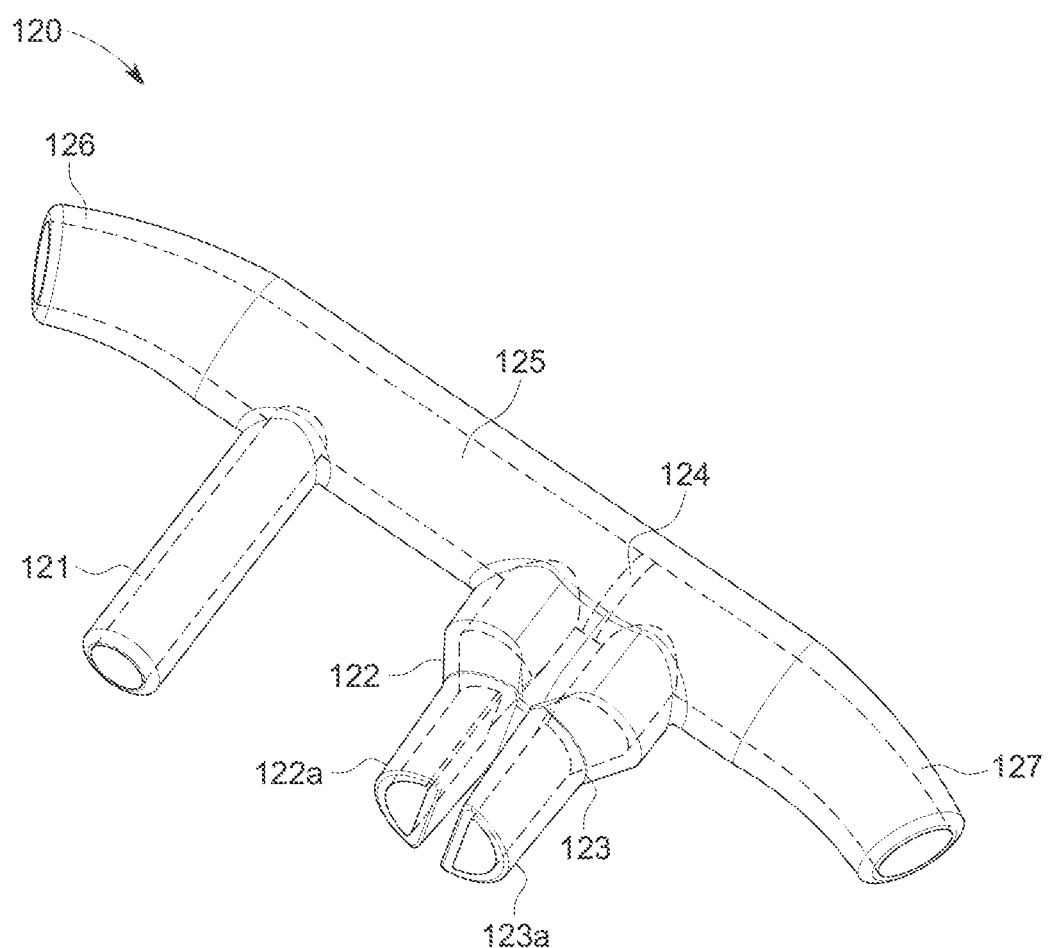
FIG. 3 is a pictorial illustration of a nasal cannula of the nasopharyngeal airway system in accordance with an illustrative embodiment.
Figure 4:
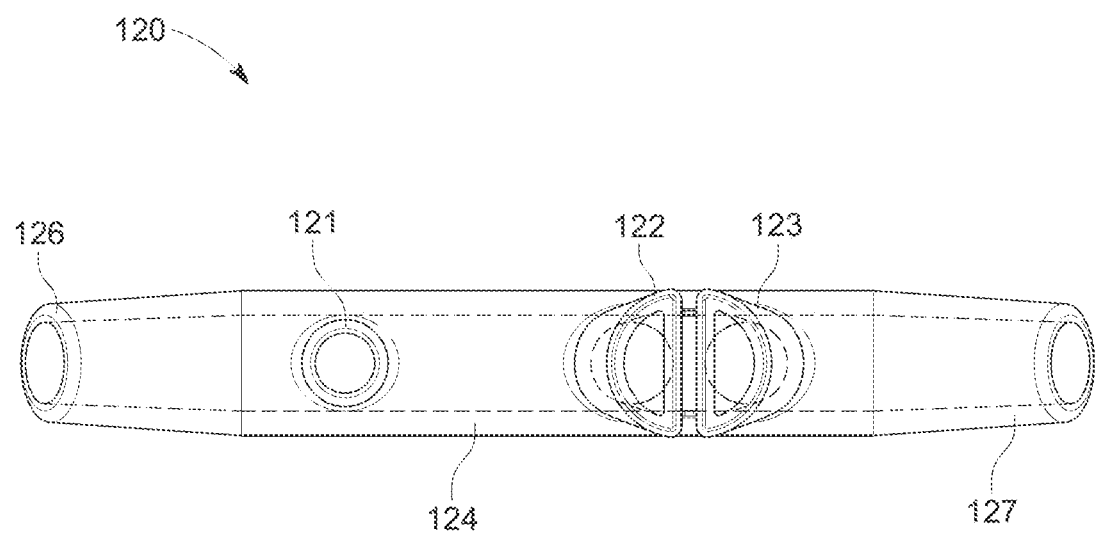
FIG. 4 is a pictorial illustration of a front view of an insertion end of the nasal cannula in accordance with an illustrative embodiment.
Figure 8:
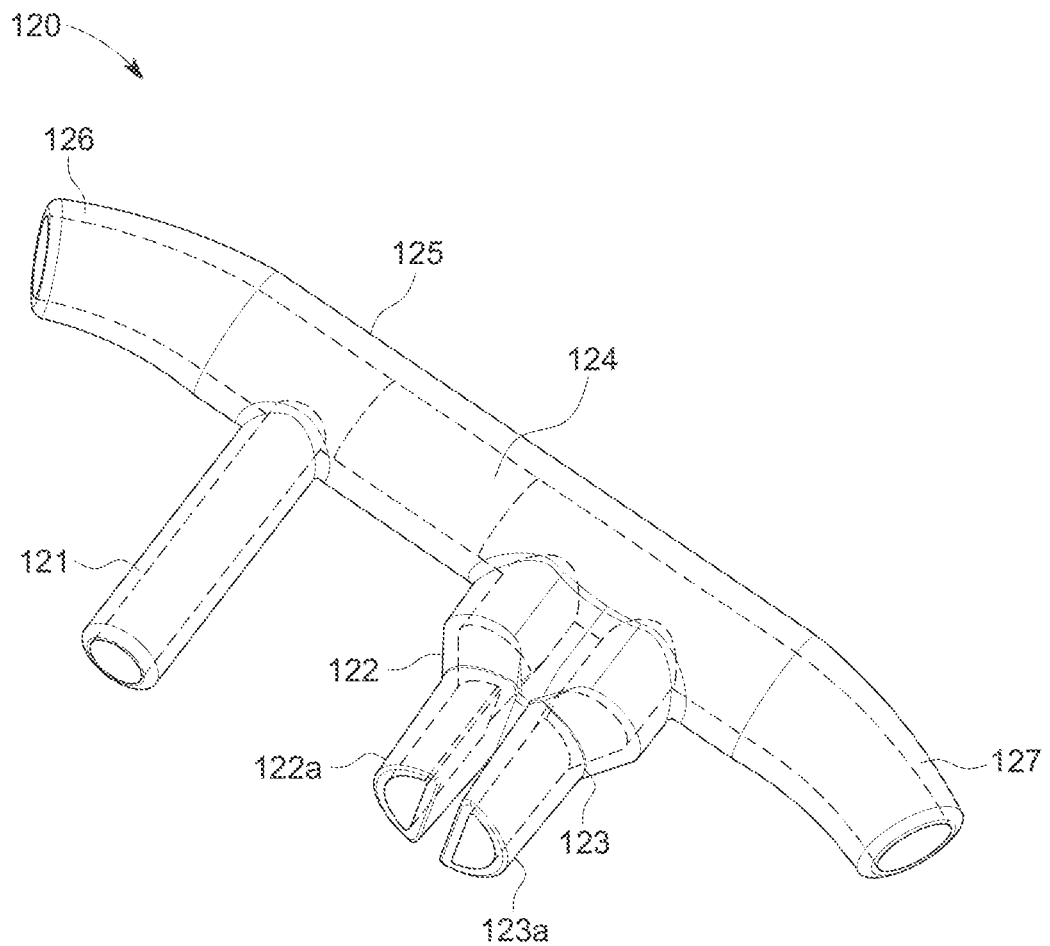
FIG. 8 is a pictorial illustration of an alternate embodiment of a nasal cannula of the nasopharyngeal airway system in accordance with an illustrative embodiment.

FIG. 3 illustrates that the tube portion 125 between the second and third prongs 122, 123, is closed off internally, which is indicated by the reference number 124. The internal closure 124 ensures that the gasses do not mix in the tube portion 125 and each prong 122, 123 is kept separate. In this example, the first and second prongs 121, 122 deliver oxygen through and the third prong 123 receives $ETCO_2$ or vice versa. It is to be understood that alternatively as shown in FIG. 8, the internal closure 124 can be formed between the first prong 121 and the second prong 122, so that both the second and third prongs 122, 123 are serving the same purpose which is separate from the purpose of the first prong 121. For example, the second and third prongs 122, 123 deliver oxygen through the nasal trumpet 110 and the first prong 121 receives $ETCO_2$ or vice versa.

As seen in the figures, the second and third prongs 122, 123 have insertion tips 122a, 123a that are inserted into the proximal end 112 of the nasal trumpet. The insertion tips 122a, 123a are separated from each other by a gap such that the insertion tips 122a, 123a can be inserted into their respective lumen in the nasal trumpet 110. The example in FIG. 3 illustrates a top perspective view of the nasal cannula 120 to provide a clear view of the gap between the insertion tips 122a, 123a. The insertion tips 122a, 123a fit into the first and second lumens 116, 118, respectively, to provide an airtight connection with the nasal cannula 120 allowing the gasses to move between the nasal trumpet 110 and the nasal cannula 120. The insertion tips 122a, 123a have a shape that is commensurate with the shape of the lumens 116, 118. As discussed above in regard to the nasal trumpet, the lumens 116, 118 can include different shapes and sizes, and thus, the insertion tips 122a, 123a on the second and third prongs 122, 123 would be commensurate with those shapes and sizes.

In the non-limiting example shown in the figures, the first prong 121 is intended to be inserted directly into a subject's nostril to deliver supplemental oxygen. The second prong 122 is also denoted as delivering oxygen, while the third prong 123 is denoted as receiving the ET $CO_2$. It is to be understood that the notations are only for the purposes of illustration and clarity, however, delivery of oxygen and receiving the ET $CO_2$ can be done through either of the adjoined prongs 122, 123. Also, as discussed above, the internal closure 124 separates the second and third prongs 122, 123 thereby separating the gasses moving through them. Also discussed as an alternative embodiment, the second and third prongs 122, 123 are not separated from each other and thereby share the same movement of gas, either delivery of oxygen or receiving of $ETCO_2$. In this embodiment, the first prong 121 is separated from the second and third prongs 122, 123 by the internal closure 124 being configured between the first prong 121 and the second prong 122.

In use, the nasal trumpet 110 is inserted through a nasal passage of a subject, wherein the distal end 114 reaches down to the posterior pharynx to bypass obstructive anatomy to give access to provide an open airway and/or secure an open airway. The proximal end 112 of the nasal trumpet 110 is positioned just outside of the subject's nares. The nasal cannula 120 is then connected to the proximal end 112 of the nasal trumpet via the second and third prongs 122, 123. The insertion tips 122a, 123a of the second and third prongs 122, 123 are inserted in to the first and second lumens 116, 118 on the proximal end 112 of the nasal insert 110. The first prong 121 of the nasal cannula 120 is inserted into the adjacent nostril and positioned just inside of the nasal vestibule. An oxygen supply is connected to the first end 126 of the tube portion 125 which delivers oxygen through the first and second prongs 121, 122. A capnometer is connected to the second end 127 which receives $ETCO_2$ from the third prong 123. Additionally, internal closure 124 separates tube portion 125 between second and third prongs 122, 124. It is to be understood, that alternatively, the oxygen supply may be connected to second end 127 of the tube portion 125 and the capnometer may be connected to the first end 126 wherein the first prong 121 of the nasal cannula 120 receives $ETCO_2$ and second and third prongs 122, 123 deliver oxygen. Additionally, internal closure 124 separates tube portion 125 between first prong 121 and second prong 122.

Alternative embodiments exist for the nasopharyngeal airway system, which can be readily appreciated by people skilled in the arts. For example, the nasopharyngeal airway system may include a nasal trumpet that is configured from a material that is radio-opaque for allowing x-ray visualization and computed tomography (CT) visualization. Alternative embodiments may also include a balloon on the distal end of the nasal trumpet or anywhere along the nasal trumper. Other non-limiting embodiments may also include integration of a suction catheter.

Accordingly, the present description provides for various embodiments for a nasopharyngeal airway system delivering oxygen while measuring $CO_2$ exhaled from a subject undergoing sedation are described. Many advantages are offered by these nasopharyngeal airway systems as described above in one or more non-limiting embodiments.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention.

The embodiments were chosen and described in order to best explain the principles of the invention and the practical application, and to enable others of ordinary skill in the art to understand the invention for various embodiments with various modifications as are suited to the particular use contemplated. The present invention according to one or more embodiments described in the present description may be practiced with modification and alteration within the spirit and scope of the appended claims. Thus, the description is to be regarded as illustrative instead of restrictive of the present invention.

What is claimed is:

1. A nasopharyngeal airway device comprising:
a nasal trumpet having two lumens, a first lumen and a second lumen extending from a proximal end to a distal end of the nasal trumpet; and
a nasal cannula having a tube portion and three prongs extending from the tube portion, wherein a first prong is insertable into a nasal cavity, and a second and third prongs abut each other and are connectable to the proximal end of the nasal trumpet, and wherein the tube portion having two open ends, a first end and a second end.

2. The nasopharyngeal airway device of claim 1, wherein the proximal end of the nasal trumpet is flared.

3. The nasopharyngeal airway device of claim 1, wherein the distal end of the nasal trumpet is configured with an angled tip.

4. The nasopharyngeal airway device of claim 1, wherein the two lumens of the nasal trumpet have an equal cross-sectional size and shape.

5. The nasopharyngeal airway device of claim 1, wherein the second and third prongs each include an insertion tip configured to snugly fit within the first lumen and the second lumen, respectively.

6. The nasopharyngeal airway device of claim 5, wherein the cross-sectional shape of the insertion tip on each of the second and third prongs is commensurate with the cross-sectional shape of the first and second lumen.

7. The nasopharyngeal airway device of claim 5, wherein the insertion tip of the second prong and the insertion tip of the third prong are spaced apart to allow the insertion tips to be inserted into their respective lumens in the nasal trumpet.

8. The nasopharyngeal airway device of claim 1, wherein the second and third prongs are adjoined at a base which is proximal to the tube portion of the nasal cannula, wherein the second and third prongs each include a separate lumen in line with their respective insertion tips to prevent mixture of gasses moving through the second and third prongs into and out of the nasal trumpet.

9. The nasopharyngeal airway device of claim 8, wherein an internal closure is configured in the tube portion between the second and third prongs to separate the gas or gasses moving through the first and second ends of the tube portion, wherein the first and second prongs are in gaseous communication with the first end of the nasal cannula, and the third prong is in gaseous communication with the second end of the nasal cannula.

10. The nasopharyngeal airway device of claim 8, wherein an internal closure is configured in the tube portion between the first prong and the second prong to separate the gas or gasses moving through the first and second ends of the tube portion, wherein the first prong is in gaseous communication with the first end of the nasal cannula, and the second and third prongs are in gaseous communication with the second end of the nasal cannula.

11. A nasopharyngeal airway device comprising,
a nasal trumpet having at least two lumens, wherein the at least two lumens extend an entire length of an internal portion extending from a proximal end to a distal end of the nasal trumpet;
a nasal cannula having a tube portion and at least three prongs extending from the tube portion, wherein:
the tube portion having a first end and a second end that are connectable to an external source each, for receiving a gas or delivering a gas; and
wherein a first prong is insertable into a nasal cavity, wherein the remaining prongs are equal in number to a number of lumens in the at least two lumens of the nasal trumpet, wherein the remaining prongs are adjacent to each other and positioned together on the tube portion and insertable into the nasal trumpet.

12. The nasopharyngeal airway device of claim 11, wherein the proximal end of the nasal trumpet is flared.

13. The nasopharyngeal airway device of claim 11, wherein the distal end of the nasal trumpet is configured with an angled tip.

14. The nasopharyngeal airway device of claim 11, wherein each lumen of the at least two lumens have lumens with an equal cross-sectional size and shape.

15. The nasopharyngeal airway device of claim 11, wherein each of the remaining prongs of the nasal cannula include an insertion tip configured to snugly fit within a respective lumen of the one or more lumens in the nasal trumpet.

16. The nasopharyngeal airway device of claim 15, wherein the cross-sectional shape of the insertion tip on each of the remaining prongs is commensurate with the cross-sectional shape of each lumen of the at least two lumens.

17. The nasopharyngeal airway device of claim 15, wherein the insertion tips of each of the remaining prongs are spaced apart to allow the insertion tips to be inserted into their respective lumens of the one or more lumens in the nasal trumpet.

18. The nasopharyngeal airway device of claim 15, wherein the insertion tip forms an airtight connection with the respective lumen of the one or more lumens in the nasal trumpet.

19. The nasopharyngeal airway device of claim 11, wherein a section of each of the remaining prongs proximal to the tube portion of the nasal cannula are adjoined together and each of the remaining prongs include a separate lumen to prevent mixture of gasses moving through the remaining prongs.

20. The nasopharyngeal airway device of claim 19, wherein if the remaining prongs include at least two prongs then a single internal closure is configured in the tube portion between a second prong and a third prong of the remaining prongs, wherein the second prong is located between the first prong and the third prong, and the third prong is immediately adjacent to the second prong, such that the first prong and the second prong are capable of sharing a gas or gasses moving through the first end of the tube portion, wherein the third prong is capable of moving a gas or gasses between the second end of the tube portion and the nasal trumpet, and the internal closure blocks the gas or gasses from moving between the first end and second end of the tube structure.

\* \* \* \* \*